United States Patent
Maruyama et al.

(10) Patent No.: US 8,822,675 B2
(45) Date of Patent: Sep. 2, 2014

(54) LOW-SUBSTITUTED HYDROXYPROPYLCELLULOSE AND SOLID PREPARATION COMPRISING THE SAME

(75) Inventors: Naosuke Maruyama, Joetsu (JP); Yasuyuki Hirama, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 294 days.

(21) Appl. No.: 13/043,113

(22) Filed: Mar. 8, 2011

(65) Prior Publication Data

US 2011/0230656 A1 Sep. 22, 2011

(30) Foreign Application Priority Data

Mar. 18, 2010 (JP) .................. 2010-062484

(51) Int. Cl.
| | |
|---|---|
| C08B 11/08 | (2006.01) |
| A61K 31/167 | (2006.01) |
| A61K 9/00 | (2006.01) |
| A61K 47/18 | (2006.01) |
| C08B 11/02 | (2006.01) |
| A61K 9/20 | (2006.01) |

(52) U.S. Cl.
CPC .............. *C08B 11/02* (2013.01); *A61K 9/2054* (2013.01); *A61K 31/167* (2013.01); *A61K 9/0056* (2013.01); *A61K 47/18* (2013.01)
USPC .................. 536/95; 536/86; 536/91; 536/124

(58) Field of Classification Search
USPC ........................ 536/86, 91, 95, 124
See application file for complete search history.

(56) References Cited

U.S. PATENT DOCUMENTS

| | | | |
|---|---|---|---|
| 7,070,805 | B2 | 7/2006 | Shimizu et al. |
| 7,399,485 | B1 | 7/2008 | Shimizu et al. |
| 2001/0010825 | A1 | 8/2001 | Shimizu et al. |
| 2003/0166918 | A1* | 9/2003 | Obara .............................. 536/86 |
| 2006/0177506 | A1* | 8/2006 | Yanai et al. .................... 424/468 |
| 2006/0182802 | A1 | 8/2006 | Shimizu et al. |
| 2007/0254031 | A1 | 11/2007 | Shimizu et al. |
| 2008/0039621 | A1* | 2/2008 | Maruyama et al. ............. 536/86 |

FOREIGN PATENT DOCUMENTS

| | | |
|---|---|---|
| EP | 2 112 169 A1 | 10/2009 |
| EP | 2 204 386 A1 | 7/2010 |

OTHER PUBLICATIONS

Kleinebudde ("Application of low substituted hydroxypropylcellulose (L-HPC) in the production of pellets using extrusion/spheronization", International Journal of Pharmaceutics, 96 (1993), pp. 119-128).*
European Search Report for Application No. 11 15 5896 dated Jul. 25, 2011.
Alvarez-Lorenzo, C. et al., *Interactions Between Hydroxypropylcelluloses and Vapour/Liquid Water*, European Journal of Pharmaceutics and Biopharamaceutics, 50, (2000), pp. 307-318.
Gohel, M. C. et al., *A Review of Co-Processed Directly Compressible Excipients*, J Pharm Phannaceut Sci, 8(1), (2005), pp. 76-93.
Quinten, T. et al., *Development of Injection Moulded Matrix Tablets Based on Mixtures of Ethylcellulose and Low-Substituted Hydroxypropylcellulose*, European Journal of Pharmaceutical Sciences, 37, (2009), pp. 207-216.
Shimizu, T. et al., *Formulation Study for Lansoprazole Fast-Disintegrating Tablet. III. Design of Rapidly Disintegrating Tablets*, Chem. Pharm. Bull. 51 (10), (2003), pp. 1121-1127.

* cited by examiner

*Primary Examiner* — Brandon Fetterolf
*Assistant Examiner* — Everett White
(74) *Attorney, Agent, or Firm* — Alston & Bird LLP

(57) ABSTRACT

Provided is nonionic and excellently stable low-substituted hydroxypropylcellulose having improved compressibility and flowability, and further having improved disintegration and texture in oral cavity. More specifically provided is low-substituted hydroxypropylcellulose having a crystallinity of 60% or less, a degree of hydroxypropoxyl substitution of 5 to 9% by weight, and an aspect ratio of less than 2.5, wherein the crystallinity is calculated based on a diffraction intensity by wide-angle X-ray diffraction measurement according to the following formula (1):

$$\text{Crystallinity}(\%) = \{(Ic - Ia)/Ic\} \times 100 \qquad (1)$$

wherein $Ic$ means a diffraction intensity at a diffraction angle $2\theta$ of $22.5°$ and $Ia$ means a diffraction intensity at a diffraction angle $2\theta$ of $18.5°$.

5 Claims, 1 Drawing Sheet

LOW-SUBSTITUTED HYDROXYPROPYLCELLULOSE AND SOLID PREPARATION COMPRISING THE SAME

BACKGROUND OF THE INVENTION

1. Field of the Invention

The present invention relates to, in pharmaceutical and food fields, low-substituted hydroxypropylcellulose which is excellent in compressibility, flowability, disintegration and texture in oral cavity, and which is water-insoluble and swellable when it absorbs water; and a rapidly disintegrating solid preparation using it.

2. Description of the Related Art

High-quality preparations have recently been required in the pharmaceutical or food field. Particularly in the pharmaceutical field, the number of unstable drugs is increasing among newly developed drugs and additives usable for them have been limited from the standpoint of their interaction. Under such a situation, low-substituted hydroxypropylcellulose is a preferable additive because it has both excellent stability due to its non-ionic nature and compressibility. However, the low-substituted hydroxypropylcellulose conventionally put on the market contains much fibrous particles and therefore lacks flowability. Accordingly, it should be used in combination with another additive having good flowability when direct tableting is applied. In addition, an amount of low-substituted hydroxypropylcellulose to be added is also limited.

In Japanese Patent Application Unexamined Publication No. 2008-133432, proposed is low-substituted hydroxypropylcellulose having improved compressibility and flowability, which has widened its application range to direct tableting. However, the disintegration of the low-substituted hydroxypropylcellulose is equal to that of the conventional one so that a further improvement in the disintegration is required.

Japanese Patent Application Unexamined Publication No. 2000-103731 discloses a rapidly disintegrating solid preparation comprising a pharmaceutical component, a sugar, and low-substituted hydroxypropylcellulose having a hydroxypropoxyl content of 5% by weight or greater but less than 7% by weight. However, the low-substituted hydroxypropylcellulose described in Japanese Patent Application Unexamined Publication No. 2000-103731 is fibrous and inferior in flowability, and has deteriorated swellability, which sometimes increases the disintegration time.

There is therefore a demand for the development of an additive excellent in compressibility, flowability, disintegration and texture in oral cavity.

SUMMARY OF THE INVENTION

The invention has been made with a view to overcoming the drawbacks of the above-described art. An object of the invention is to provide a non-ionic and excellently stable low-substituted hydroxypropylcellulose having improved compressibility and flowability, and further having improved disintegration and texture in oral cavity.

As a result of intensive investigation for achieving the object, the invention provides low-substituted hydroxypropylcellulose having a crystallinity of 60% or less, a degree of hydroxypropoxyl substitution of 5 to 9% by weight, and an aspect ratio of less than 2.5, wherein the crystallinity is calculated based on the diffraction intensity by wide-angle X-ray diffraction measurement in accordance with the following formula (1):

$$\text{Crystallinity}(\%) = \{(Ic - Ia)/Ic\} \times 100 \tag{1}$$

wherein Ic means a diffraction intensity at a diffraction angle $2\theta$ of $22.5°$ and Ia means a diffraction intensity at a diffraction angle $2\theta$ of $18.5°$.

The invention also provides a method for preparing low-substituted hydroxypropylcellulose comprising at least the steps of: mixing powdered pulp with an aqueous solution of sodium hydroxide at a weight ratio (a) of sodium hydroxide to anhydrous cellulose in the pulp of 0.15 to 0.50 and a weight ratio (b) of sodium hydroxide to water of 0.45 to 0.60 to obtain an alkali cellulose; reacting the alkali cellulose with propylene oxide to obtain low-substituted hydroxypropylcellulose; and subjecting the resulting low-substituted hydroxypropylcellulose to compaction and subsequent grind in a grinder, or to simultaneous compaction and grind in a grinder.

According to the preparation method of the invention, low-substituted hydroxypropylcellulose superior in compressibility, flowability and disintegration to the low-substituted hydroxypropylcelluloses prepared by the conventional method can be provided.

Since the low-substituted hydroxypropylcellulose of the invention has high compressibility, high flowability and excellence in disintegration and texture in oral cavity, it can produce a solid preparation having a high tablet hardness and excellent disintegration in a filed such as pharmaceutical and food. Particularly, a solid preparation of the invention has excellent disintegration so that it can be used for the treatment or prevention of various diseases as an oral rapidly disintegrating tablet that the elderly or children can take easily without water.

DETAILED DESCRIPTION OF THE PREFERRED EMBODIMENTS

Figure 1:
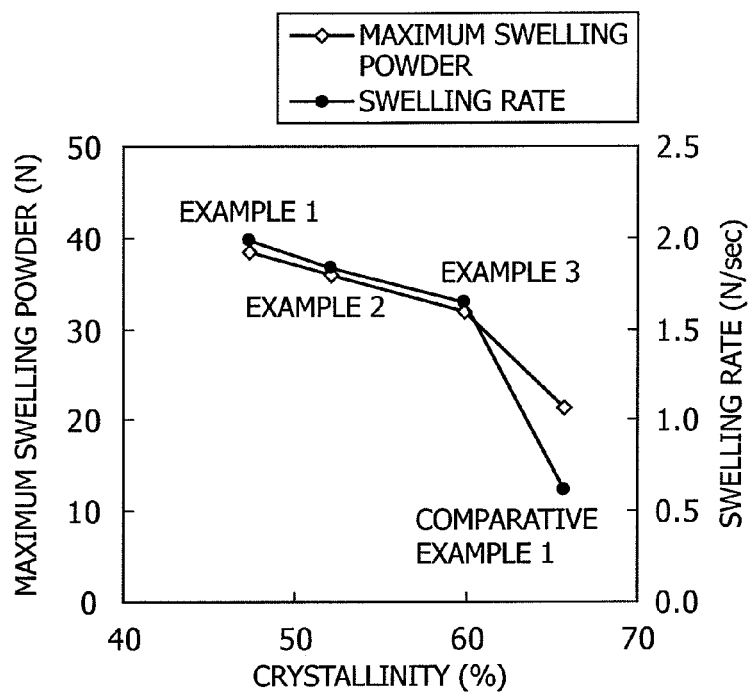
FIG. 1 shows the maximum swelling power and swelling rate of low-substituted hydroxypropylcelluloses obtained in Examples 1 to 3 and Comparative Example 1.

The degree of hydroxypropoxyl substitution of the low-substituted hydroxypropylcellulose of the invention is preferably 5 to 9% by weight, more preferably 7 to 9% by weight. The degree of hydroxypropoxyl substitution can be determined based on the quantitative analysis of low-substituted hydroxypropylcellulose in the Japanese Pharmacopoeia. When the degree is less than 5% by weight, an intended rapidly disintegrating preparation may not be produced because the resulting low-substituted hydroxypropylcellulose may not swell well during water absorption and may have reduced disintegration. When the degree is more than 9% by weight, a swelling rate decreases in spite of an increase in a swelling amount and an intended rapidly disintegrating preparation may not be produced. Accordingly there is an optimal range for the degree of substitution.

It is known that the wide-angle X-ray diffraction pattern of natural cellulose, raw material of low-substituted hydroxypropylcellulose, has a crystal structure of Cellulose I type and a strong diffraction peak is observed at diffraction angles $2\theta$ of $14.7°$, $16.5°$ and $22.5°$ in wide-angle X-ray diffraction. In particular, the 002 plane characteristically shows the highest peak at a diffraction angle $2\theta$ of $22.5°$ (which will hereinafter be designated as "Ic"). Segal et al. proposes in Text.

Res. J. 29, 786, (1959) a method of determining a crystallinity from this diffraction peak intensity of the 002 plane and a diffraction peak intensity of an amorphous fraction at 2θ of 18.5° (which will hereinafter be designated as "Ia"). The crystallinity (%) in the invention can be determined according to the following formula (I):

$$\text{Crystallinity}(\%)=\{(Ic-Ia)/Ic\}\times 100 \quad (1)$$

The wide-angle X-ray diffraction is a method of analyzing a crystal structure by making use of a phenomenon that X-rays are diffracted by crystal lattices. Commercially available diffractometers can be used. For example, "MX-Labo" (trade name; product of Bruker AXS) can be used.

The crystallinity of the low-substituted hydroxypropylcellulose of the invention is 60% or less. Low-substituted hydroxypropylcellulose having a crystallinity exceeding 60% cannot provide an intended rapidly disintegrating preparation even if it has a degree of hydroxypropoxyl substitution within the above range because they have a reduced swelling power and swelling rate. Although no particular limitation is imposed on the lower limit of the crystallinity, the lower limit of the crystallinity of the low-substituted hydroxypropylcellulose is considered to be approximately 40%. It is because that of commonly-used regenerated celluloses such as rayon is said to be about 40%.

In a crystal region, firm hydrogen bonding prevents penetration of water into molecules, allowing only the surface thereof to adsorb the water. In an amorphous region, absorbed water penetrates into the molecule and widens the molecular chain of the low-substituted hydroxypropylcellulose, leading to a stronger swelling power. Further, intermolecular bonding is weaker in the amorphous region than in the crystal region so that water molecules are introduced into the amorphous region more rapidly and a swelling rate is higher. This means that crystallinity is an important property having an influence on the swelling property of a disintegrant. As the crystallinity becomes lower and the amorphous region becomes wider, the swelling power and swelling rate increase.

The maximum swelling power in the invention is preferably 25N or greater, more preferably 30N or greater. When the maximum swelling power is less than 25N, it may take much time for disintegration, a drug may not be released rapidly, and an intended medicinal efficacy may not be exhibited. As the swelling power of a disintegrant is higher, a tablet or granule comprising the disintegrant shows better medicinal efficacy because of a short disintegration time and rapid release of the drug. No particular limitation is therefore imposed on the upper limit, but it may be about 50N. The swelling power can be determined by using a texture analyzer such as "TA-XT plus" (trade name; product of Stable Micro Systems, Ltd.).

The swelling rate is preferably 1 N/sec or greater, more preferably 1.5 N/sec or greater. When the swelling rate is less than 1 N/sec, it may take much time for disintegration. As the swelling rate is greater, the disintegration time of tablet or granule can be decreased so that no particular limitation is imposed on the upper limit, but it may be about 5 N/sec.

Shimizu et al. report in Chem. Pharm. Bull. 51(10), 1121-1127 (2003) that the palatability of an additive to oral rapidly disintegrating tablets is important and the palatability becomes better as the degree of hydroxypropoxyl substitution of low-substituted hydroxypropylcellulose becomes lower. Shimizu et al. explain the reason as follows. When the low-substituted hydroxypropylcellulose absorbs water and swells therewith, much water is exhausted so that a recipient has an unpleasant dry texture such as paper eating. There is a correlation between this phenomenon (the unpleasant dry texture) and the viscosity of the aqueous dispersion of low-substituted hydroxypropylcellulose. As the degree of hydroxypropoxyl substitution becomes lower, the viscosity of the aqueous dispersion becomes lower so that the texture in oral cavity is improved.

The viscosity of an aqueous dispersion of the low-substituted hydroxypropylcellulose of the invention is preferably 50 mPa·s or less. When the viscosity is more than 50 mPa·s, the texture in oral cavity may be deteriorated. The viscosity of an aqueous dispersion of the low-substituted hydroxypropylcellulose is determined in the following manner: 25 g of sample is added to 225 g of pure water at 20° C., the resulting mixture is stirred for 10 minutes at a rate of about 200 rpm by using a stirring blade to prepare an aqueous dispersion having a concentration of 10% by weight, and measured is the value two minutes after operation of a Brookfield type viscometer at a rotational speed of 30 rpm at 20° C.

The present inventors have found that not only the degree of hydroxypropoxyl substitution but also an aspect ratio, which is a ratio of long diameter to short diameter, of the low-substituted hydroxypropylcellulose particles has an influence on the palatability in oral cavity. This means that even if the degree of hydroxypropoxyl substitution is the same, fibrous particles having a higher aspect ratio are likely to be inferior in texture in oral cavity because the aqueous dispersion of them has a high viscosity.

In addition, the aspect ratio has an influence on not only the viscosity of an aqueous dispersion of the low-substituted hydroxypropylcellulose and texture in oral cavity but also the flowability of the powders.

The low-substituted hydroxypropylcellulose of the invention has an aspect ratio of less than 2.5, preferably 2.3 or less. Conventional low-substituted hydroxypropylcellulose particles contain many fibrous particles derived from the shape of the raw material pulp. As described in pages 5 to 6 in the brochure of L-HPC published by Shin-Etsu Chemical Co., Ltd., the conventional low-substituted hydroxypropylcellulose has an aspect ratio ranging from 2.5 to 5.0. Low-substituted hydroxypropylcellulose containing many long fibers and having an aspect ratio of 2.5 or greater lacks powder flowability so that another additive having good flowability should be used together when direct tableting is applied. In addition, there may be a limitation on an amount of the low-substituted hydroxypropylcellulose to be added.

The aspect ratio is determined by measuring the long diameter and the short diameter with a common optical microscope at a magnification of about 100, and calculating the ratio of the long diameter to the short diameter. About 50 to 200 particles are measured and then averaged.

The particle size distribution of the powders is an indicator influencing on the compressibility and flowability of the particles. The particle size distribution can be measured by using a particle size measuring method with laser diffraction. For example, "HELOS & RODOS" (trade name; product of Japan Laser Corp.) can be used for the measurement.

The low-substituted hydroxypropylcellulose of the present invention has an average particle size of preferably 10 to 80 μm, more preferably 20 to 60 μm, still more preferably 30 to 60 μm in order to keep high compressibility, high flowability and excellent disintegration. Low-substituted hydroxypropylcellulose powder having an average particle size of less than 10 μm may have an increased agglomeration property, reduced flowability and also reduced disintegration. The powder having an average particle size of more than 80 μm may have reduced compressibility because a sufficient specific surface area cannot be secured.

A preferable preparation method of the low-substituted hydroxypropylcellulose in the invention will hereinafter be described.

The raw material of the low-substituted hydroxypropylcellulose of the invention may include material pulp and linter pulp. The pulp in powder form is used. For obtaining pulp powder, any grinding method may be employed. The average particle size of the pulp powder is preferably from 60 to 300 µm. It may be industrially inefficient to prepare pulp powder having an average particle size less than 60 µm, while pulp powder having an average particle size exceeding 300 µm may be inferior in miscibility with an aqueous solution of sodium hydroxide.

In a step of preparing alkali cellulose, alkali cellulose may be prepared preferably by adding an aqueous solution of sodium hydroxide dropwise or in an atomization-like manner to the pulp powder and mixing them. In this step, the strong crystal structure of the cellulose is destroyed by the aqueous solution of sodium hydroxide and mercerization proceeds. The mercerization improves the reactivity in the subsequent etherification of the alkali cellulose.

The alkali cellulose may be prepared preferably by mixing in an internal stirring type reactor and then subjected to an etherification reaction in the reactor. Alternatively, the alkali cellulose prepared in a mixer may be placed in a reactor and then subjected an etherification reaction.

The alkali cellulose is composed of cellulose, sodium hydroxide and water. It has been found that the content of sodium hydroxide and the content of water, each in the alkali cellulose, have an influence on not only the etherification reaction efficiency but also the swelling characteristics of the final product.

With regards to the optimum composition of the alkali cellulose in the invention, a weight ratio of sodium hydroxide to anhydrous cellulose (pulp after removal of water) is from 0.15 to 0.50, preferably from 0.19 to 0.50. When the weight ratio is less than 0.15, the low-substituted hydroxypropylcellulose thus obtained may have a high crystallinity, a reduced swelling power, and reduced disintegration. When the weight ratio is more than 0.50, the low-substituted hydroxypropylcellulose thus obtained has a reduced swelling rate and a reduced etherification efficiency due to an increase in the weight portion of sodium hydroxide, which may lead to industrial inefficiency.

A weight ratio of sodium hydroxide to water {(weight of sodium hydroxide)/(weight of water)} is from 0.45 to 0.60, preferably form 0.50 to 0.60. It is necessary to control the weight ratio of sodium hydroxide to anhydrous cellulose and the weight ratio of sodium hydroxide to water to fall within the above ranges, respectively, in order to achieve the optimum composition of the alkali cellulose. When the weight ratio of sodium hydroxide to water is less than 0.45 or more than 0.60, the low-substituted hydroxypropylcellulose thus obtained has a high crystallinity, a reduced swelling power and swelling rate, and a reduced disintegration.

The concentration of the aqueous solution of sodium hydroxide to be used for the preparation of the alkali cellulose is preferably from 20 to 50% by weight.

In a step of carrying out the etherification reaction, the alkali cellulose is placed in a reactor and preferably after purging with nitrogen, the reactor is charged with propylene oxide as an etherification agent. Propylene oxide is used preferably in an amount of about 0.1 to 1.0 mol per mol of an anhydrous glucose unit. Preferably, the reaction temperature may be about 40 to 80° C. and the reaction time may be about 1 to 5 hours.

The etherification reaction step may be followed by a dissolution step if necessary. The dissolution step comprises dissolving in water or hot water a part or whole of the crude reaction product obtained by the etherification reaction. An amount of water or hot water differs depending on an amount of the crude reaction product to be dissolved. The amount of water in which the whole of the crude reaction product is dissolved may be typically 0.5 to 10 in terms of the weight ratio of the amount of water to the low-substituted hydroxypropylcellulose in the crude reaction product.

In consideration of the burden in the below-mentioned washing/dehydration step and a further improvement in the compressibility of the low-substituted cellulose ether, it is more preferred not to perform this dissolution step.

A subsequent neutralization step may preferably comprise introducing the crude reaction product into water or hot water containing an acid wherein the amount of acid is equivalent of that of the sodium hydroxide which is used as a catalyst and remains in the reaction product. Alternatively, the neutralization step may comprise adding, to the reaction product, water or hot water containing an equivalent amount of an acid. Examples of the acid used for neutralization may include mineral acids such as hydrochloric acid, sulfuric acid and nitric acid, and organic acids such as formic acid and acetic acid.

The next washing/dehydration step may comprise dehydrating the neutralized product preferably by centrifugal separation, filtration under reduced pressure or filtration under pressure, while washing it preferably with water or hot water. The low-substituted hydroxypropylcellulose in the cake thus obtained by dehydration is in fibrous form similar to the form of the raw material pulp. From the standpoint of compressibility, grinding of the cellulose in fibrous form can yield a product having a high specific surface area and a high binding property.

A drying step may comprise drying the dehydrated product preferably at 60 to 120° C. with a dryer such as fluidized bed dryer or a drum dryer.

A grinding step may comprise subjecting the dried product obtained in the above manner to the compaction and grind by using a grinder, which is compaction and subsequent grind, or simultaneous compaction and grind. In the compaction and grind, a grinder such as a roller mill, a ball mill, a bead mill or a mortar-type grinder can be used. The roller mill is a grinder in which a roller or ball rolls over while compressing/shearing a grinding target on the wall of the mill by a centrifugal force or gravity load accompanying rotational movement of the roller or ball. The roller mill may include "IS mill" manufactured by Ishikawajima-Harima Heavy Industries Co., Ltd., "VX mill" manufactured by Kurimoto, Ltd., "MS roller mill" manufactured by MASUNO SEISAKUSHO LTD. A ball mill is a grinder which uses, as a grinding medium, a steel ball, a magnetic ball, a cobblestone or an analog thereto. The ball mill may include a vibration ball mill manufactured by Chuo Kakohki Co., Ltd., a ball mill manufactured by Kurimoto, Ltd., a tube mill manufactured by Otsuka Iron Works and a planetary ball mill manufactured by FRITSCH. A bead mill is similar to the ball mill, but is different in that the diameter of the ball is smaller and acceleration of the ball can be increased further by high-speed rotation of the internal portion of the device. The bead mill may include a bead mill manufactured by Ashizawa Fintech Ltd. A mortar-type mill is a grinder which can grind powder with a mortar rotating at a high speed and at a narrow clearance. The mortar-type mill may include "Serendipiter" manufactured by MASUKO SANGYO CO., LTD.

These grinders can grind down long fibrous particles and reduce the number of them. As a result, the powder thus obtained has a small aspect ratio and acquires excellent flowability. In addition, the compaction and grind micro fibrillate a portion of the fibrous particles, thereby increasing the specific surface area of them. This is effective for improving the compressibility.

The low-substituted hydroxypropylcellulose of the invention can be used as a binder or disintegrant for solid preparations such as tablets and granules. The tablets can be obtained by any of the manufacturing methods such as dry direct tableting, wet agitation-granulation tableting, fluidized bed granulation tableting and dry granulation tableting.

The dry direct tableting is a method comprising the steps of dry-mixing the low-substituted hydroxypropylcellulose powder, a drug, the other excipient, a lubricant and the like and then tableting the resulting mixture. The dry direct tableting method offers high productivity because it is a simple manufacturing method without a granulation step. The wet agitation-granulation tableting is a method comprising the steps of granulating the low-substituted hydroxypropylcellulose powder, a drug and the other excipient with water or a water-soluble binder solution in a high-speed agitation granulator, drying the resulting granulate, mixing the dried granulate with a lubricant, and then tableting the mixture. The wet agitation-granulation tableting method can provide tablets having uniform drug content. The fluidized bed granulation tableting is a method comprising the steps of granulating the low-substituted hydroxypropylcellulose powder, a drug and the other excipient with water or a water-soluble binder solution in a fluidized bed granulator, drying the resulting granulate, mixing the dried granulate with a lubricant, and then tableting the resulting mixture. The fluidized bed granulation tableting method can provide tablets having uniform drug content, similarly to the wet agitation-1-granulation tableting method. The dry granulation tableting is a method comprising the steps of granulating the low-substituted hydroxypropylcellulose, a drug, the other excipient and the like by compression and then tableting the resulting granulate. The dry granulation tableting method is effective for drugs sensitive to water or solvents.

The low-substituted hydroxypropylcellulose of the invention can be used as a binder for granules or as a disintegrant. The granules can be obtained by any of the above methods such as wet agitation-granulation, fluidized bed granulation and dry granulation.

Columnar granules obtained through extrusion granulation or a granulate obtained through extrusion granulation may be made spherical by using a marumelizer (spheroidization machine). Alternatively, layering can be carried out by scattering mixed powders of the low-substituted hydroxypropylcellulose powder, a drug powder, the other excipient and the like to a true spherical core made of sugar or the like, while spraying a binder solution thereto.

In addition, the low-substituted hydroxypropylcellulose of the invention can also be used for oral rapidly disintegrating tablets which have been actively developed in recent years and which disintegrate rapidly in oral cavity even without water or with a small amount of water. They are effective for the elderly or children having difficulty in swallowing the conventional dosage forms.

The oral rapidly disintegrating preparation of the invention can be manufactured by mixing the low-substituted hydroxypropylcellulose of the invention, an active ingredient, and a sugar such as lactose or sugar alcohol (such as sorbitol, mannitol, maltitol, reduced starch saccharide, xylitol, reduced palatinose or erythritol), mixing the resulting mixture with a lubricant, and the direct-tableting the obtained mixture. Alternatively, the oral rapidly disintegrating preparation of the invention can be manufactured by carrying out wet agitation-granulation, fluidized bed granulation or the like to form granules comprising the low-substituted hydroxypropylcellulose of the invention, an active component, and a sugar such as lactose or sugar alcohol (such as sorbitol, mannitol, maltitol, reduced starch saccharide, xylitol, reduced palatinose, or erythritol), and then tableting the granules.

The content of the active ingredient differs depending on the nature of the drug, but may be preferably 0.1 to 30% by weight, more preferably 1 to 20% by weight in the entirety of the preparation.

The content of the sugar may be preferably 5 to 97% by weight, more preferably 10 to 90% by weight in the entire preparation.

The content of the low-substituted hydroxypropylcellulose may be preferably 1 to 30% by weight, more preferably 5 to 10% by weight in the entire preparation.

The drug to be used for the preparation comprising the low-substituted hydroxypropylcellulose of the invention may include, but not limited to, a drug for the central nervous system, a drug for the circulatory system, a drug for the respiratory system, a drug for the digestive system, antibiotics, chemotherapeutic agents, a drug for metabolic system and a vitamin drug.

The drug for the central nervous system may include diazepam, idebenone, aspirin, ibuprofen, paracetamol, naproxen, piroxicam, diclofenac, indomethacin, sulindac, lorazepam, nitrazepam, phenyloin, acetaminophen, ethenzamide and ketoprofen.

The drug for the circulatory system may include molsidomine, vinpocetine, propranolol, methyldopa, dipyridamole, furosemide, triamterene, nifedipine, atenolol, spironolactone, metoprolol, pindolol, captopril and isosorbide nitrate.

The drug for the respiratory system may include amlexanox, dextromethorphan, theophylline, pseudoephedrine, salbutamol and guaifenesin.

The drug for the digestive system may include a benzimidazole-based drug having antiulcer activity such as 2-{[3-methyl-4-(2,2,2-trifluoroethoxy)-2-pyridyl]methylsulfinyl}benzimidazole and 5-methoxy-2-[(4-methoxy-3,5-dimethyl-2-pyridyl)methylsulfinyl]benzimidazole, cimetidine, ranitidine, pancreatin, bisacodyl and 5-aminosalicylic acid.

The antibiotics and chemotherapeutic agents may include cephalexin, cefaclor, cefradine, amoxicillin, pivampicillin, bacampicillin, dicloxacillin, erythromycin, erythromycin stearate, lincomycin, doxycycline and trimethoprim/sulfamethoxazole.

The drug for metabolic system may include serrapeptase, lysozyme chloride, adenosine triphosphate, glibenclamide and potassium chloride.

The vitamin drug may include vitamin B1, vitamin B2, vitamin B6 and vitamin C.

The method for manufacturing the oral rapidly disintegrating preparation in the invention does not require any special apparatus or special technique. The preparation can be obtained in an ordinary employed method by using an ordinarily employed granulator or tableting machine. Thus, the method has broad utility, which is achieved by the low-substituted hydroxypropylcellulose of the invention to be used as a binder and a disintegrant.

The rapidly disintegrating solid preparation of the invention may comprise a various type of additive used for producing a common preparation insofar as it does not disturb the rapid disintegration or strength of the preparation. It may be added in an amount used for producing a common preparation. The additive may include a binder, and acidulant, a foaming agent, an artificial sweetener, a flavor, a lubricant, a coloring agent, a stabilizer, an excipient and a disintegrant.

The binder may include hydroxypropylcellulose, hydroxypropylmethyl cellulose, crystalline cellulose, a starch, polyvinyl pyrrolidone, powdered gum arabic, gelatin and pullulan. Two or more of these binders mixed at an appropriate ratio may be used. It may be preferred for producing the oral rapid-disintegrating preparation to use the low-substituted hydroxypropylcellulose as a binder without using the above water-soluble binder, because a solid preparation having a higher strength can be obtained while keeping an excellent oral rapidly disintegrating property.

EXAMPLES

The present invention will hereinafter be described in detail based on Examples. It should not be construed that the invention is limited to or by them.

Example 1

A 10-L internal stirring type reactor was charged with 829 g of pulp powder (800 g on the anhydrous basis). The reactor was further charged with 621.8 g of an aqueous 35% by weight solution of sodium hydroxide. They were mixed at 45° C. for 30 minutes to produce alkali cellulose having a weight ratio of sodium hydroxide to anhydrous cellulose of 0.272 and a weight ratio of sodium hydroxide to water of 0.502.

After nitrogen purging, 108 g (0.135 part by weight based on the anhydrous cellulose) of propylene oxide was added to the resulting alkali cellulose, followed by a reaction at a jacket temperature of 60° C. to obtain a crude reaction product of low-substituted hydroxypropylcellulose.

After 327 g of glacial acetic acid was added to 10 L of warm water in a reactor, the crude reaction product of low-substituted hydroxypropylcellulose obtained above was added thereto for neutralization. The neutralized product was then washed with hot water in a batch vacuum filter. The resulting dehydrated product was then dried in a fluidized bed dryer at an intake air temperature of 80° C. until an outlet air temperature became 60° C.

The dried product was then ground for 120 minutes in a vibration ball mill, followed by filtration through a sieve having an opening of 75 μm to obtain low-substituted hydroxypropylcellulose having a degree of hydroxypropoxyl substitution of 8.4% by weight (the number of moles of substituent per anhydrous glucose unit: 0.194) and an average particle size of 47 μm as measured by laser diffraction.

Example 2

A 10-L internal stirring type reactor was charged with 829 g of pulp powder (800 g on the anhydrous basis). The reactor was further charged with 631.6 g of an aqueous 37% by weight solution of sodium hydroxide. They were mixed at 45° C. for 30 minutes to produce alkali cellulose having a weight ratio of sodium hydroxide to anhydrous cellulose of 0.292 and a weight ratio of sodium hydroxide to water of 0.547.

After nitrogen purging, 104 g (0.13 part by weight based on the anhydrous cellulose) of propylene oxide was added to the resulting alkali cellulose, followed by a reaction at a jacket temperature of 60° C. to obtain a crude reaction product of low-substituted hydroxypropylcellulose.

After 351 g of glacial acetic acid was added to 10 L of warm water in a reactor, the crude reaction product of low-substituted hydroxypropylcellulose obtained above was added thereto for neutralization. The neutralized product was then washed with hot water in a batch vacuum filter. The resulting dehydrated product was then dried in a fluidized bed dryer at an intake air temperature of 80° C. until an outlet air temperature became 60° C.

The dried product was then ground for 120 minutes in a vibration ball mill, followed by filtration through a sieve having an opening of 75 μm to obtain low-substituted hydroxypropylcellulose having a degree of hydroxypropoxyl substitution of 8.2% by weight (the number of moles of substituent per anhydrous glucose unit: 0.189) and an average particle size of 49 μm as measured by laser diffraction.

Example 3

A 10-L internal stirring type reactor was charged with 829 g of pulp powder (800 g on the anhydrous basis). The reactor was further charged with 473.7 g of an aqueous 33% by weight solution of sodium hydroxide. They were mixed at 45° C. for 30 minutes to produce alkali cellulose having a weight ratio of sodium hydroxide to anhydrous cellulose of 0.195 and a weight ratio of sodium hydroxide to water of 0.451.

After nitrogen purging, 100 g (0.125 part by weight based on the anhydrous cellulose) of propylene oxide was added to the resulting alkali cellulose, followed by a reaction at a jacket temperature of 60° C. to obtain a crude reaction product of low-substituted hydroxypropylcellulose.

After 234.5 g of glacial acetic acid was added to 10 L of warm water in a reactor, the crude reaction product of low-substituted hydroxypropylcellulose obtained above was added thereto for neutralization. The neutralized product was then washed with hot water in a batch vacuum filter. The resulting dehydrated product was then dried in a fluidized bed dryer at an intake air temperature of 80° C. until an outlet air temperature became 60° C.

The dried product was then ground for 120 minutes in a vibration ball mill, followed by filtration through a sieve having an opening of 75 μm to obtain low-substituted hydroxypropylcellulose having a degree of hydroxypropoxyl substitution of 7.8% by weight (the number of moles of substituent per anhydrous glucose unit: 0.179) and an average particle size of 50 μm as measured by laser diffraction.

Example 4

A 10-L internal stirring type reactor was charged with 829 g of pulp powder (800 g on the anhydrous basis). The reactor was further charged with 576.7 g of an aqueous 39% by weight solution of sodium hydroxide. They were mixed at 45° C. for 30 minutes to produce alkali cellulose having a weight ratio of sodium hydroxide to anhydrous cellulose of 0.281 and a weight ratio of sodium hydroxide to water of 0.591.

After nitrogen purging, 80 g (0.10 part by weight based on the anhydrous cellulose) of propylene oxide was added to the resulting alkali cellulose, followed by a reaction at a jacket temperature of 60° C. to obtain a crude reaction product of low-substituted hydroxypropylcellulose.

After 337.4 g of glacial acetic acid was added to 10 L of warm water in a reactor, the crude reaction product of low-substituted hydroxypropylcellulose obtained above was added thereto for neutralization. The neutralized product was then washed with hot water in a batch vacuum filter. The resulting dehydrated product was then dried in a fluidized bed dryer at an intake air temperature of 80° C. until an outlet air temperature became 60° C.

The dried product was then ground for 120 minutes in a vibration ball mill, followed by filtration through a sieve having an opening of 75 μm to obtain low-substituted hydroxypropylcellulose having a degree of hydroxypropoxyl substitution of 6.2% by weight (the number of moles of substituent per anhydrous glucose unit: 0.141) and an average particle size of 47 μm as measured by laser diffraction.

Example 5

A 10-L internal stirring type reactor was charged with 829 g of pulp powder (800 g on the anhydrous basis). The reactor was further charged with 1105.3 g of an aqueous 35% by weight solution of sodium hydroxide. They were mixed at 45° C. for 30 minutes to produce alkali cellulose having a weight ratio of sodium hydroxide to anhydrous cellulose of 0.484 and a weight ratio of sodium hydroxide to water of 0.518.

After nitrogen purging, 108 g (0.135 part by weight based on the anhydrous cellulose) of propylene oxide was added to the resulting alkali cellulose, followed by a reaction at a jacket temperature of 60° C. to obtain a crude reaction product of low-substituted hydroxypropylcellulose.

After 581 g of glacial acetic acid was added to 10 L of warm water in a reactor, the crude reaction product of low-substituted hydroxypropylcellulose obtained above was added thereto for neutralization. The neutralized product was then washed with hot water in a batch vacuum filter. The resulting dehydrated product was then dried in a fluidized bed dryer at an intake air temperature of 80° C. until an outlet air temperature became 60° C.

The dried product was then ground for 120 minutes in a vibration ball mill, followed by filtration through a sieve having an opening of 75 μm to obtain low-substituted hydroxypropylcellulose having a degree of hydroxypropoxyl substitution of 6.8% by weight (the number of moles of substituent per anhydrous glucose unit: 0.155) and an average particle size of 45 μm as measured by laser diffraction.

Comparative Example 1

A 10-L internal stirring type reactor was charged with 829 g of pulp powder (800 g on the anhydrous basis). The reactor was further charged with 138.2 g of an aqueous 35% by weight solution of sodium hydroxide. They were mixed at 45° C. for 30 minutes to produce alkali cellulose having a weight ratio of sodium hydroxide to anhydrous cellulose of 0.06, a weight ratio of water to anhydrous cellulose of 0.149, and a weight ratio of sodium hydroxide to water of 0407.

After nitrogen purging, 120 g (0.15 part by weight based on the anhydrous cellulose) of propylene oxide was added to the resulting alkali cellulose, followed by a reaction at a jacket temperature of 60° C. to obtain a crude reaction product of low-substituted hydroxypropylcellulose.

After 72 g of glacial acetic acid was added to 10 L of warm water in a reactor, the crude reaction product of low-substituted hydroxypropylcellulose obtained above was added thereto for neutralization. The neutralized product was then washed with hot water in a batch vacuum filter. The resulting dehydrated product was then dried in a fluidized bed dryer at an intake air temperature of 80° C. until an outlet air temperature became 60° C.

The dried product was then ground for 120 minutes in a vibration ball mill, followed by filtration through a sieve having an opening of 75 μm to obtain low-substituted hydroxypropylcellulose having a degree of hydroxypropoxyl substitution of 8.7% by weight (the number of moles of substituent per anhydrous glucose unit: 0.201) and an average particle size of 51 μm as measured by laser diffraction.

Comparative Example 2

In a similar manner to that described in Example of Japanese Patent Application Unexamined Publication No. 2000-103731, wood pulp was immersed in an aqueous 49% by weight sodium of hydroxide solution and compressed to produce alkali cellulose having a weight ratio of sodium hydroxide to anhydrous cellulose of 0.491 and a weight ratio of sodium hydroxide to water of 0897.

A 10-L internal stirring type reactor was charged with 1632 g of the alkali cellulose thus obtained (800 g in terms of anhydrous cellulose). After nitrogen purging, 80 g (0.1 part by weight based on the anhydrous cellulose) of propylene oxide was added thereto, followed by a reaction at a jacket temperature of 60° C. to obtain a crude reaction product of low-substituted hydroxypropylcellulose.

After 4000 g of warm water and 58 g of glacial acetic acid were placed in a batch kneader, the whole amount of the crude product was added thereto and dissolved therein. Then, 1772 g of 30% by weight acetic acid was added thereto at a fixed rate and neutralization precipitation was carried out. The neutralized product was then washed with hot water in a batch vacuum filter. The resulting dehydrated product was then dried in a fluidized bed dryer at an intake air temperature of 80° C. until an outlet air temperature became 60° C.

The dried product was then ground in a high-speed rotation impact grinder, followed by filtration through a sieve having an opening of 75 μm to obtain low-substituted hydroxypropylcellulose having a degree of hydroxypropoxyl substitution of 5.8% by weight (the number of moles of substituent per anhydrous glucose unit: 0.131) and an average particle size of 45 μM as measured by laser diffraction.

Comparative Example 3

In a similar manner to that described in Example of Japanese Patent Application Unexamined Publication No. 2008-133432, a 10-L internal stirring type reactor was charged with 829 g of pulp powder (800 g on the anhydrous basis); it was then further charged with 323.6 g of an aqueous 26% by weight solution of sodium hydroxide. They were mixed at 45° C. for 30 minutes to produce alkali cellulose having a weight ratio of sodium hydroxide to anhydrous cellulose of 0.105, a weight ratio of water to anhydrous cellulose of 0.336, and a weight ratio of sodium hydroxide to water of 0.313.

After nitrogen purging, 135 g (0.169 part by weight based on the anhydrous cellulose) of propylene oxide was added to the resulting alkali cellulose, followed by a reaction at a jacket temperature of 60° C. to obtain a crude reaction product of low-substituted hydroxypropylcellulose.

After 126 g of glacial acetic acid was added to 10 L of warm water in a reactor, the crude reaction product of low-substituted hydroxypropylcellulose obtained above was added thereto for neutralization. The neutralized product was then washed with hot water in a batch vacuum filter. The resulting dehydrated product was then dried in a fluidized bed dryer at an intake air temperature of 80° C. until an outlet air temperature became 60° C.

The dried product was then ground in a planetary ball mill for 60 minutes, followed by filtration through a sieve having an opening of 75 μm to obtain low-substituted hydroxypropylcellulose having a degree of hydroxypropoxyl substitution of 11.8% by weight (the number of moles of substituent per anhydrous glucose unit: 0.28) and an average particle size of 45 μm as measured by laser diffraction.

The low-substituted hydroxypropylcelluloses obtained in Example 1 to 5 and Comparative Examples 1 to 3 were evaluated for their crystallinity, aspect ratio, viscosity of an aqueous dispersion, maximum swelling power, swelling rate, and texture in oral cavity by using the methods described below and the results are shown in Table 1.

<Measurement of Crystallinity>

It was measured by using a wide-angle powder X-ray diffractometer "MX-Labo" (trade name; product of Bruker AXS) under the following conditions: Cu-Kα radiation (30 kV, 40 mA), a scanning angle range 2θ: 10° to 40°, and a scanning rate of 2°/min.

$$\text{Crystallinity}(\%) = \{(Ic-Ia)/Ic\} \times 100 \quad (1)$$

speed: 2.0 mm/sec, test speed: 1.0 mm/sec, post-test speed: 10 mm/sec, force: 20 g, trigger force: 5 g <Measurement of Viscosity of Aqueous Dispersion>

After 25 g of sample was added to 225 g of pure water at 20° C., the resulting mixture was stirred for 10 minutes to prepare an aqueous 10% by weight dispersion. The viscosity of the resulting aqueous dispersion was measured after operation of a Brookfield viscometer at 20° C. for 2 minutes at a rotation speed of 30 rpm.

<Evaluation of Texture in Oral Cavity>

Each of six healthy adults was administered with 0.5 g of sample and asked to evaluate the smoothness of it in oral cavity. It was evaluated with the number of the adults who felt that the sample was powdery and dry.

TABLE 1

|  |  | Example 1 | Example 2 | Example 3 | Example 4 | Example 5 | Comp. Ex. 1 | Comp. Ex. 2 | Comp. Ex 3 |
|---|---|---|---|---|---|---|---|---|---|
| Preparation conditions | wt. ratio sodium hydroxide [1] | 0.272 | 0.292 | 0.195 | 0.281 | 0.484 | 0.060 | 0.491 | 0.105 |
|  | wt ratio of NaOH to water [2] | 0.502 | 0.547 | 0.451 | 0.591 | 0.518 | 0.407 | 0.897 | 0.313 |
|  | grinding | Compaction-grind | Compaction-grind | Compaction-grind | Compaction-grind | Compaction-grind | Compaction-grind | Compaction-grind | Compaction-grind |
| Property | degree of hydroxypropoxyl substitution (% by weight) | 8.4 | 8.2 | 7.8 | 6.2 | 6.8 | 8.7 | 5.8 | 11.8 |
|  | crystallinity (%) | 47.3 | 52.1 | 59.9 | 48.3 | 44.9 | 65.7 | 63.2 | 61.5 |
|  | maximum swelling power(N) | 39 | 36 | 32 | 28 | 30 | 21 | 15 | 24 |
|  | swelling rate (N/second) | 1.98 | 1.84 | 1.64 | 2.80 | 3.10 | 0.61 | 0.50 | 0.55 |
|  | aspect ratio | 2.2 | 2.3 | 2.4 | 2.4 | 2.3 | 2.2 | 3.8 | 2.4 |
|  | viscosity of aqueous dispersion (mPa · s) | 34 | 38 | 42 | 34 | 35 | 41 | 72 | 110 |
|  | texture in oral cavity | 0/6 | 0/6 | 0/6 | 0/6 | 0/6 | 0/6 | 2/6 | 6/6 |

[1] a weight ratio of sodium hydroxide to anhydrous cellulose.
[2] a weight ratio of sodium hydroxides to water.

The crystallinity was determined according to the above formula (I) from the diffraction peak intensity of the 002 plane at 2θ=22.5° (designated as Ic) and a diffraction peak intensity of the amorphous fraction at 2θ=18.5° (designated as Ia).

<Measurement of Aspect Ratio>

A long diameter and a short diameter of 100 particles were measured using a digital microscope "VHX-200" (trade name; product of Keyence) at a magnification of 75. The aspect ratios were calculated and an average was found. The aspect ratio means a ratio of a long diameter to a short diameter.

<Measurements of Maximum Swelling Power and Swelling Rate>

The swelling power was measured using a texture analyzer "TA-XT plus" (trade name; product of SMS) under the following conditions and the value that became constant after an increase of the swelling power with the passage of time was determined as the maximum swelling power. In addition, the time required for reaching the maximum swelling power was measured and the swelling rate was calculated according to the following formula:

Swelling rate (N/sec)=(maximum swelling power)/ (time required for reaching the maximum swelling power)

Amount of sample: 1 g, measurement program: HLDD, water absorption cross-sectional area: 5.31 cm2, pretest The low-substituted hydroxypropylcelluloses obtained in Examples 1 to 5 showed a higher maximum swelling power and a higher swelling rate than those obtained in Comparative Examples 1 to 3.

The maximum swelling power and the swelling rate were compared between the low-substituted hydroxypropylcelluloses obtained in Examples 1 to 3 and Comparative Example 1 in which the low-substituted hydroxypropylcelluloses were similar in the degree of hydroxypropoxyl substitution but different in crystallinity. As shown in FIG. 1, those obtained in Examples 1 to 3 having a crystallinity of 60% or less exhibited a higher maximum swelling power and a higher swelling rate than that obtained in Comparative Example 1. It is evident that the crystallinity is an important property which determines the maximum swelling power and the swelling rate.

In addition, the low-substituted hydroxypropylcelluloses obtained in Examples 1 to 5 by using a compaction and grind system have a smaller aspect ratio, superior in flowability, a lower viscosity as an aqueous dispersion, and superior in texture in oral cavity compared with that obtained in Comparative Example 2 (corresponding to Japanese Patent Application Unexamined Publication No. 2000-103731) obtained by using an impact grind system. The low-substituted hydroxypropylcellulose obtained in Comparative Example 3 (corresponding to Japanese Patent Application Unexamined Publication No. 2008-133432) by using a compaction and grind system has therefore a small aspect ratio. However, because it has a degree of hydroxypropoxyl substitution as high as 11.8%, its aqueous dispersion has a high viscosity and the texture in oral cavity is inferior.

Example 6

An oral rapidly disintegrating tablet was prepared by carrying out fluidized bed granulation with the low-substituted hydroxypropylcellulose of Example 1 as a binder and a disintegrant.

An aqueous dispersion of the low-substituted hydroxypropylcellulose obtained in Example 1, which the dispersion had the following composition, was sprayed to the following powder under the following conditions.

TABLE 2

| Composition for Granulation | | | | |
|---|---|---|---|---|
| Powder | acetaminophen | 15 g | 5 parts by weight |
| | 200 mesh lactose | 285 g | 95 parts by weight |
| Liquid | low-substituted hydroxypropylcellulose | 15 g | 5 parts by weight |
| | 200 mesh lactose | 15 g | 5 parts by weight |
| | purified water | 270 g | 90 parts by weight |

| Conditions for Granulation | |
|---|---|
| Granulator | Multiplex MP-01 by Powlex Corporation |
| Intake air temp. | 60° C. |
| Outlet air temp. | 25 to 27° C. |
| Air flow | 0.6 m³/min |
| Spray rate | 15 g/min |
| Air pressure for spray | 150 kPa |
| Subsequent drying | dried at an intake air temperature of 60° C. until an outlet air temperature became 45° C. |

After 0.5 part by weight of magnesium stearate was added to 100 parts by weight of the granules thus obtained and mixed, continuous tableting was performed under the following conditions.

TABLE 3

| Tableting Conditions | |
|---|---|
| Tableting Machine | rotary tableting machine produced by Kikusui Seisakujo Ltd. |
| Tablet Size | 200 mg/tablet, 8 mm-D, 12 mm-R |
| Tableting Pressure | 5.0 kN to 12.5 kN |
| Tableting Speed | 40 rpm |

Figure 2:
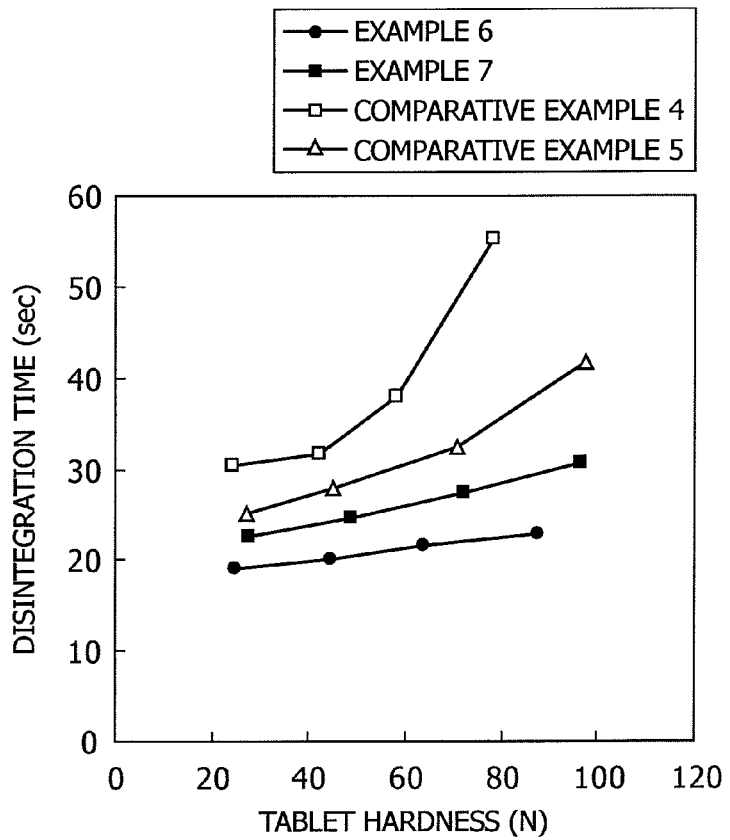
FIG. 2 shows the tablet hardness and disintegration time of low-substituted hydroxypropylcelluloses obtained in Examples 5 and 6 and Comparative Examples 4 to 6.

The hardness of the tablet obtained under each of tableting pressures was measured using an automatic tablet testing system for physical parameters "TM-5" (trade name; product of Kikusui Seisakujo Ltd.). A disintegration time of the tablet in pure water was evaluated in accordance with Disintegration Test of the Japanese Pharmacopoeia. The results are shown in FIG. 2. In addition, tablet was formed by adjusting the tableting pressure to allow the tablet hardness to fall within a range of 70 to 75 N. The tablet thus obtained was evaluated for disintegration time in oral cavity and texture in oral cavity based on the following method. The results are shown in Table 4.

<Measurement of Disintegration Time in Oral Cavity and Texture in Oral Cavity>

Each of six healthy adults was administered with the tablet; the time required for disintegration of the tablet in oral cavity was measured; and the values for the time were collected and averaged. In addition, they were asked to evaluate the smoothness of it in oral cavity.

Example 7

An oral rapidly disintegrating tablet was prepared by performing fluidized bed granulation with the low-substituted hydroxypropylcellulose of Example 3 as a binder and a disintegrant.

Under conditions similar to those employed in Example 6 except for use of low-substituted hydroxypropylcellulose of Example 3 instead of that of Example 1, granulation and tableting were performed.

The hardness of the tablet obtained under each of tableting pressures was measured using an automatic tablet testing system for physical parameters "TM-5" (trade name; product of Kikusui Seisakujo Ltd.) and a disintegration time in pure water was evaluated in accordance with Disintegration Test of the Japanese Pharmacopoeia. The results are shown in Table 2. In addition, the tablet was formed by adjusting the tableting pressure to allow the tablet hardness to fall within a range of from 70 to 75 N. The tablet thus obtained was evaluated for disintegration time in oral cavity and texture in oral cavity. The results are shown in Table 4.

Comparative Example 4

An oral rapidly disintegrating tablet was manufactured by carrying out fluidized bed granulation with the low-substituted hydroxypropylcellulose of Comparative Example 2 as a binder and a disintegrant.

Under conditions similar to those employed in Example 6 except for use of low-substituted hydroxypropylcellulose of Comparative Example 2 instead of that of Example 1, granulation and tableting were performed.

The hardness of the tablet obtained under each of tableting pressures was measured using an automatic tablet testing system for physical parameters "TM-5" (trade name; product of Kikusui Seisakujo Ltd.) and a disintegration time in pure water was evaluated in accordance with Disintegration Test of the Japanese Pharmacopoeia. The results are shown in Table 2. In addition, the tablet was formed by adjusting the tableting pressure to allow the tablet hardness to fall within a range of from 70 to 75 N. The tablet thus obtained was evaluated for disintegration time in oral cavity and texture in oral cavity. The results are shown in Table 4.

Comparative Example 5

An oral rapidly disintegrating tablet was prepared by carrying out fluidized bed granulation with the low-substituted hydroxypropylcellulose of Comparative Example 3 as a binder and a disintegrant.

Under conditions similar to those employed in Example 6 except for use of low-substituted hydroxypropylcellulose of Comparative Example 3 instead of that of Example 1, granulation and tableting were performed.

The hardness of the tablet obtained under each of tableting pressures was measured using an automatic tablet testing system for physical parameters "TM-5" (trade name; product of Kikusui Seisakujo Ltd.) and a disintegration time in pure water was evaluated in accordance with Disintegration Test of the Japanese Pharmacopoeia. The results are shown in Table 2. In addition, the tablet was formed by adjusting the tableting pressure to allow the tablet hardness to fall within a range of from 70 to 75 N. The tablet thus obtained was evaluated for disintegration time in oral cavity and texture in oral cavity. The results are shown in Table 4.

It is evident in FIG. 2 that the tablets obtained in Examples 6 and 7 have a higher swelling power and a higher swelling rate than the tablets obtained in Comparative Examples 4 and 5 so that they show excellent rapid disintegration even at high tablet hardness. It is evident in Table 4 that the tablets obtained in Examples 6 and 7 are useful as oral rapidly disintegrating tablets because they are disintegrated in oral cavity more rapidly and superior in texture in oral cavity compared with those obtained in Comparative Examples 4 and 5.

It is considered that the low-substituted hydroxypropylcellulose of the invention shows excellent disintegration because it has a degree of hydroxypropoxyl substitution of 5 to 9% by weight and a crystallinity of 60% or less and therefore has a high swelling power and a high swelling rate. It is also considered that it is excellent in texture in oral cavity because it has an aspect ratio of less than 2.5.

TABLE 4

| | disintegration time in oral cavity (seconds) | texture in oral cavity |
|---|---|---|
| Example 6 | 18 | No one had powder-like feeling. Good. |
| Example 7 | 22 | No one had powder-like feeling. Good. |
| Comp. Ex. 4 | 55 | Two of six had powder-like feeling. |
| Comp. Ex. 5 | 41 | Five of six had powder-like feeling. |

The invention claimed is:

1. Low-substituted hydroxypropylcellulose having a crystallinity of 60% or less, a degree of hydroxypropoxyl substitution of 5 to 9% by weight, an average particle size of 10 to 80 μm and an aspect ratio of less than 2.5, wherein the crystallinity is calculated based on a diffraction intensity by wide-angle X-ray diffraction measurement in accordance with the following formula (1):

$$\text{Crystallinity}(\%) = \{(Ic-Ia)/Ic\} \times 100 \quad (1)$$

wherein Ic means a diffraction intensity at a diffraction angle 2θ of 22.5° and Ia means a diffraction intensity at a diffraction angle 2θ of 18.5°.

2. The low-substituted hydroxypropylcellulose according to claim 1, wherein a 10% by weight aqueous dispersion of the low-substituted hydroxypropylcellulose has a viscosity of 50 mPa·s or less at 20° C.

3. A solid preparation comprising the low-substituted hydroxypropylcellulose as claimed in claim 1.

4. The solid preparation according to claim 3, which is an orally and rapidly disintegrating solid preparation.

5. A method for preparing the low-substituted hydroxypropylcellulose comprising at least the steps of:

mixing powdered pulp and an aqueous solution of sodium hydroxide at a weight ratio of sodium hydroxide to anhydrous cellulose of 0.15 to 0.50 and a weight ratio of sodium hydroxide to water of 0.45 to 0.60 to obtain an alkali cellulose;

reacting the alkali cellulose with propylene oxide to obtain low-substituted hydroxypropylcellulose; and subjecting the low-substituted hydroxypropylcellulose to compaction and subsequent grind in a grinder, or to simultaneous compaction and grind in a grinder, wherein the low-substituted hydroxypropylcellulose has a crystallinity of 60% or less, a degree of hydroxypropoxyl substitution of 5 to 9% by weight, and an aspect ratio of less than 2.5, wherein the crystallinity is calculated based on a diffraction intensity by wide-angle X-ray diffraction measurement in accordance with the following formula (1):

$$\text{Crystallinity}(\%) = \{(Ic-Ia)/Ic\} \times 100 \quad (1)$$

wherein Ic means a diffraction intensity at a diffraction angle 2θ of 22.5° and Ia means a diffraction intensity at a diffraction angle 2θ of 18.5°.

* * * * *